United States Patent [19]

Petrzilka et al.

[11] Patent Number: 4,583,826
[45] Date of Patent: Apr. 22, 1986

[54] PHENYLETHANES

[75] Inventors: Martin Petrzilka, Kaiseraugst; Martin Schadt, Seltisberg, both of Switzerland

[73] Assignee: Hoffmann-La Roche Inc., Nutley, N.J.

[21] Appl. No.: 432,212

[22] Filed: Oct. 1, 1982

[30] Foreign Application Priority Data

| Oct. 19, 1981 [CH] | Switzerland | 6572/81 |
| Mar. 19, 1982 [CH] | Switzerland | 1725/82 |
| Jul. 8, 1982 [CH] | Switzerland | 4172/82 |

[51] Int. Cl.[4] .................. C09K 3/34; G02F 1/13; C07C 1/26; C07C 5/03; C07C 13/28; C07C 2/86
[52] U.S. Cl. .................. 350/350 R; 252/299.61; 252/299.5; 252/299.63; 252/299.66; 350/350 S; 585/20; 585/25
[58] Field of Search .................. 252/299.63, 299.66, 252/299.5, 299.61; 585/25, 20; 350/350 R, 350 S

[56] References Cited

U.S. PATENT DOCUMENTS

| 4,035,056 | 7/1977 | Coates et al. | 252/299.66 |
| 4,130,502 | 10/1977 | Eidenschink et al. | 252/299.63 |
| 4,261,651 | 4/1981 | Gray et al. | 252/299.63 |
| 4,330,426 | 5/1982 | Eidenschink et al. | 252/299.63 |
| 4,331,552 | 5/1982 | Eidenschink et al. | 252/299.63 |
| 4,337,999 | 7/1982 | Funada et al. | 252/299.63 |
| 4,393,258 | 7/1983 | Sato et al. | 252/299.63 |
| 4,400,293 | 8/1983 | Romer et al. | 252/299.63 |
| 4,419,263 | 12/1983 | Praefcke et al. | 252/299.63 |
| 4,431,853 | 2/1984 | Sato et al. | 252/299.63 |
| 4,439,015 | 3/1984 | Rich et al. | 252/299.63 |
| 4,455,443 | 6/1984 | Takatsu et al. | 252/299.63 |
| 4,460,770 | 7/1984 | Petrzilka et al. | 252/299.63 |
| 4,472,592 | 9/1984 | Takatsu et al. | 252/299.63 |
| 4,482,472 | 11/1984 | Carr et al. | 252/299.5 |
| 4,514,044 | 4/1985 | Gunjima et al. | 252/299.63 |

FOREIGN PATENT DOCUMENTS

| 56113 | 7/1982 | European Pat. Off. | 252/299.63 |
| 72204 | 2/1983 | European Pat. Off. | 252/299.63 |
| 84194 | 7/1983 | European Pat. Off. | 252/299.63 |
| 3003256 | 8/1980 | Fed. Rep. of Germany | 252/299.63 |
| 3006666 | 9/1981 | Fed. Rep. of Germany | 252/299.63 |
| 57-163324 | 10/1982 | Japan | 252/299.63 |
| 58-10529 | 1/1983 | Japan | 252/299.63 |
| 58-8023 | 1/1983 | Japan | 252/299.63 |
| 58-8022 | 1/1983 | Japan | 252/299.63 |
| 59-110630 | 6/1984 | Japan | 252/299.63 |
| 59-110631 | 6/1984 | Japan | 252/299.63 |
| 2065104 | 6/1981 | United Kingdom | 252/299.63 |
| 2086385 | 5/1982 | United Kingdom | 252/299.63 |
| 2092146 | 8/1982 | United Kingdom | 252/299.63 |
| 2093057 | 8/1982 | United Kingdom | 252/299.63 |
| 2092169 | 8/1982 | United Kingdom | 252/299.61 |

OTHER PUBLICATIONS

Praefcke, K., et al, Chem. Zeitung, vol. 104, No. 9, pp. 269–271 (1980).
Carr et al., Lecture on "New Liquid Crystalline Materials Derived from Bicyclooctane and Cyclohexane" at the 4th International LC Conference of Socialist Countries in Tiflis (Oct. 5–8, 1981).
Gray, Lecture on "Relationship Between Chemical Structure and Properties for Low Molecular Weight Liquid Crystals" at Santa Margherita Ligure, Italy (Jun., 1981).
U.S. Ser. No. 341,926, 1/82 Rich et al.

*Primary Examiner*—Teddy S. Gron
*Attorney, Agent, or Firm*—Jon S. Saxe; Bernard S. Leon; George W. Johnston

[57] ABSTRACT

Compounds of the formula

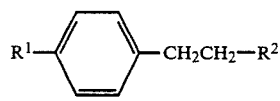

I wherein $R^1$ signifies trans-4-alkylcyclohexyl, 4'-alkyl-4-biphenylyl, p-(trans-4-alkylcyclohexyl)phenyl, 2-(trans-4-alkylcyclohexyl)ethyl or p-[2-(trans-4-alkylcyclohexyl)ethyl]phenyl and $R^2$ signifies trans-4-alkylcyclohexyl; or $R^1$ signifies trans-4-alkylcyclohexyl and $R^2$ signifies p-(trans-4-alkylcyclohexyl)phenyl, p-[2-(trans-4-alkylcyclohexyl)ethyl]phenyl or 4'-(trans-4-alkylcyclohexyl)-4-biphenylyl; or $R^1$ signifies p-alkylphenyl and $R^2$ signifies p-[2-(trans-4-alkylcyclohexyl)ethyl]phenyl, and the alkyl groups in the substituents $R^1$ and $R^2$ are straight-chain groups containing 1 to 7 carbon atoms, liquid crystalline mixtures which contain these compounds and their use for electro-optical purposes are described.

The novel compounds of formula I are especially valuable as components in liquid crystal mixtures and themselves have liquid crystalline properties.

17 Claims, No Drawings

PHENYLETHANES

BACKGROUND OF THE INVENTION

1. Field of the Invention

This invention relates to liquid crystalline compounds and mixtures.

2. Description of the Art

Liquid crystals recently have gained considerable importance primarily as dielectrics in indicating devices, since the optical properties of such substances can be influenced by an applied voltage. Electro-optical indicating devices which utilize liquid crystal cells are well known to the person skilled in the art and can be based on various effects such as, for example, dynamic scattering, deformation of aligned phases (DAP type), the Schadt-Helfrich effect (rotation cell), the "guest-host effect" or a cholestericnematic type phase transition.

Liquid crystals must satisfy a number of requirements in order to be suitable as dielectrics for electro-optical indicating devices. For example, the liquid crystals must have a high chemical stability towards environmental factors (e.g. heat, air, moisture and the like), must be photochemically stable and colorless, must have short response times, must not be too high a viscosity, must have nematic or cholesteric-type mesophase in all temperature ranges in which the liquid crystal cell is to be operated, and must give a good contrast. Other properties such as, for example, the threshold potential, the dielectric anisotropy and the electrical conductivity must fulfill different conditions depending on the type of cell which is used.

Since, in general, it is not possible to achieve all desired and to some extent contradictory properties with a single compound, attempts have been made to use several components so as to produce optimal properties for the particular application. In this case it is, however, important that the components undergo no chemical reactions with one another and can be mixed well. Further, ideally the mixtures should have no or small smectic mesophases.

In the present invention, novel liquid crystalline compounds and mixtures have been found which permit the further improvement of the properties of liquid crystalline dielectrics.

SUMMARY OF THE INVENTION

The present invention concerns phenylethanes of the formula

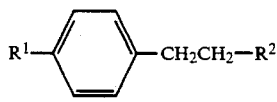

wherein $R^1$ is trans-4-alkylcyclohexyl, 4'-alkyl-4-biphenylyl, p-(trans-4-alkylcyclohexyl)phenyl, 2-(trans-4-alkylcyclohexyl)ethyl or p-[2-(trans-4-alkylcyclohexyl)ethyl]phenyl and $R^2$ is trans-4-alkylcyclohexyl; or $R^1$ is trans-4-alkylcyclohexyl and $R^2$ is p-(trans-4-alkylcyclohexyl)phenyl, p-[2-(trans-4-alkylcyclohexyl)ethyl]phenyl or 4'-(trans-4-alkylcyclohexyl)-4-biphenylyl; or $R^1$ is p-alkylphenyl and $R^2$ is p-[2-(trans-4-alkylcyclohexyl)ethyl]phenyl, and the alkyl groups in the substituents $R^1$ and $R^2$ are straight-chain groups of 1 to 7 carbon atoms.

The invention is also concerned with the manufacture of the compounds of formula I above, liquid crystalline mixtures which contain compounds of formula I above as well as their use for electro-optical purposes.

It has now been found that the compounds provided by the invention are very well suited as components of liquid crystalline mixtures, since they surprisingly at the same time have large mesophase ranges with high clearing points as well as low viscosities and accordingly short response times. Moreover, the melting points are often very considerably super-coolable. Further, the compounds provided by the invention have small absolute values of the dielectric anisotropies and generally a nematic and/or smectic mesophase. Furthermore, they have an excellent chemical and photochemical stability and are colourless. The compounds provided by the invention can be widely used, since they have a good miscibility with other liquid crystals and since liquid crystals having nematic or cholesteric mesophases can be manufactured readily by mixing the present compounds with other liquid crystalline and/or non-liquid crystalline compounds. On the basis of the aforementioned properties they are especially suitable for increasing the clearing points of mixtures having low viscosities, since in this case the viscosity is not increased or is increased only insignificantly.

DETAILED DESCRIPTION OF THE INVENTION

The present invention is concerned with novel tri-, tetra- and pentacyclic phenylethanes of the formula

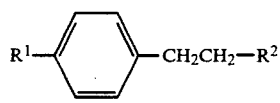

wherein $R^1$ is trans-4-alkylcyclohexyl, 4'-alkyl-4-biphenylyl, p-(trans-4-alkylcyclohexyl)phenyl, 2-(trans-4-alkylcyclohexyl)ethyl or p-[2-(trans-4-alkylcyclohexyl)ethyl]phenyl and $R^2$ is trans-4-alkylcyclohexyl; or $R^1$ is trans-4-alkylcyclohexyl and $R^2$ is p-(trans-4-alkylcyclohexyl)phenyl, p-[2-(trans-4-alkylcyclohexyl)ethyl]phenyl or 4'-(trans-4-alkylcyclohexyl)-4-biphenylyl; or $R^1$ is p-alkylphenyl and $R^2$ is p-[2-(trans-4-alkylcyclohexyl)ethyl]phenyl, and the alkyl groups in the substituents $R^1$ and $R^2$ are straight-chain groups of 1 to 7 carbon atoms.

The invention is also concerned with the manufacture of the compounds of formula I above, liquid crystalline mixtures which contain compounds of formula I above as well as their use for electro-optical purposes.

The compounds in accordance with the invention contain one or two terminal trans-4-alkylcyclohexyl groups as well as 1-3 p-phenylene groups and one or two ethylene groups.

Unless otherwise stated, "alkyl" denotes a straight-chain alkyl group of 1 to 12 carbon atoms or a branched-chain alkyl group of 1 to 12 carbon atoms. Exemplary straight-chain alkyl groups are methyl, ethyl, propyl, butyl, pentyl, hexyl, heptyl octyl, nonyl, decyl, undecyl and dodecyl. Exemplary branched-chain alkyl groups are isopropyl, isobutyl, sec-butyl, 1-methylbutyl, 2-methylbutyl 3-methylpentyl, 4-methylhexyl and isopentyl. Lower alkyl denotes straight-chain and branched-chain alkyl groups of 1 to 5 carbon atoms.

The term "alkoxy" as well as any other groups in the specification containing "alkyl" denote moieties in which their "alkyl" portions are as defined previously. In particular, straight-chain alkoxy groups denote moieties having a straight-chain alkyl portion as previously defined.

The term "halogen" denotes fluorine, chlorine, bromine or iodine.

The term "alkali metal" denotes sodium, potassium or lithium.

The inventive compounds are very well suited as components of liquid crystalline mixtures, since they surprisingly at the same time have large mesophase ranges with high clearing points as well as low viscosities and accordingly short response times. Moreover, the melting points are often very considerably supercoolable. Further, the compounds provided by the invention have small absolute values of the dielectric anisotropies and generally a nematic and/or smectic mesophase. Furthermore, they have an excellent chemical and photochemical stability and are colorless. The compounds provided by the invention can be widely used, since they have a good miscibility with other liquid crystals and since liquid crystals having nematic or cholesteric mesophases can be manufactured readily by mixing the present compounds with other liquid crystalline and/or non-liquid crystalline compounds. On the basis of the aforementioned properties they are especially suitable for increasing the clearing points of mixtures having low viscosities, since in this case the viscosity is not increased or is increased only insignificantly.

Those compounds of formula I in which the sum of the carbon atoms in the two terminal alkyl groups of the substituents $R^1$ and $R^2$ is 5 to 10 are preferred. Those compounds of formula I in which $R^1$ signifies trans-4-alkyl-cyclohexyl, 4'-alkyl-4-biphenylyl or p-(trans-4-alkylcyclohexyl)phenyl and $R^2$ signifies trans-4-alkylcyclohexyl; or $R^1$ signifies trans-4-alkylcyclohexyl and $R^2$ signifies 4'-(trans-4-alkylcyclohexyl)-4-biphenylyl are also preferred.

The following are examples of preferred compounds of formula I:

1-[2-(Trans-4-propylcyclohexyl)ethyl]-4-(trans-4-ethylcyclohexyl)benzene,
1-[2-(trans-4-propylcyclohexyl)ethyl]-4-(trans-4-propylcyclohexyl)benzene,
1-[2-(trans-4-propylcyclohexyl)ethyl]-4-(trans-4-pentylcyclohexyl)benzene,
1-[2-(trans-4-propylcyclohexyl)ethyl]-4-(trans-4-heptylcyclohexyl)benzene,
1-[2-(trans-4-butylcyclohexyl)ethyl]-4-(trans-4-pentylcyclohexyl)benzene,
1-[2-(trans-4-pentylcyclohexyl)ethyl]-4-(trans-4-propylcyclohexyl)benzene,
1-[2-(trans-4-pentylcyclohexyl)ethyl]-4-(trans-4-butylcyclohexyl)benzene,
1-[2-(trans-4-pentylcyclohexyl)ethyl]-4-(trans-4-pentylcyclohexyl)benzene,
4-(trans-4-ethylcyclohexyl)-4'-[2-(trans-4-propylcyclohexyl)ethyl]biphenyl,
4-(trans-4-propylcyclohexyl)-4'-[2-(trans-4-propylcyclohexyl)ethyl]biphenyl,
4-(trans-4-butylcyclohexyl)-4'-[2-(trans-4-pentylcyclohexyl)ethyl]biphenyl,
4-(trans-4-pentylcyclohexyl)-4'-[2-(trans-4-propylcyclohexyl)ethyl]biphenyl,
4-(trans-4-pentylcyclohexyl)-4'-[2-(trans-4-butylcyclohexyl)ethyl]biphenyl,
4-(trans-4-pentylcyclohexyl)-4'-[2-trans-4-pentylcyclohexyl)ethyl]biphenyl,
4-(trans-4-heptylcyclohexyl)-4'-[2-(trans-4-propylcyclohexyl)ethyl]biphenyl,
1-[2-(trans-4-ethylcyclohexyl)ethyl]-4-[2-(trans-4-propylcyclohexyl)ethyl]benzene,
1,4-bis[2-(trans-4-propylcyclohexyl)ethyl]benzene,
1-[2-(trans-4-butylcyclohexyl)ethyl]-4-[2-(trans-4-pentylcyclohexyl)ethyl]benzene,
1-[2-(trans-4-pentylcyclohexyl)ethyl]-4-[2-(trans-4-propylcyclohexyl)ethyl]benzene,
1,4-bis[2-(trans-4-pentylcyclohexyl)ethyl]benzene,
1-[2-(trans-4-heptylcyclohexyl)ethyl]-4-[2-(trans-4-propylcyclohexyl)ethyl]benzene,
4-[2-(trans-4-ethylcyclohexyl)ethyl]-4'-[2-(trans-4-propylcyclohexyl)ethyl]biphenyl,
4,4'-bis[2-(trans-4-propylcyclohexyl)ethyl]biphenyl,
4-[2-(trans-4-butylcyclohexyl)ethyl]-4'-[2-(trans-4-pentylcyclohexyl)ethyl]biphenyl,
4-[2-(trans-4-pentylcyclohexyl)ethyl]-4'-[2-(trans-4-propylcyclohexyl)ethyl]biphenyl,
4,4'-bis[2-(trans-4-pentylcyclohexyl)ethyl]biphenyl,
4-[2-(trans-4-heptylcyclohexyl)ethyl]-4'-[2-(trans-4-propylcyclohexyl)ethyl]biphenyl,
4-(trans-4-ethylcyclohexyl)-4'-(trans-4-propylcyclohexyl)-1,1'-ethylenedibenzene,
4,4'-bis(trans-4-propylcyclohexyl)-1,1'-ethylenedibenzene,
4-(trans-4-butylcyclohexyl)-4'-(trans-4-pentylcyclohexyl)-1,1'-ethylenebidenzene,
4-(trans-4-pentylcyclohexyl)-4'-(trans-4-propylcyclohexyl)-1,1'-ethylenedibenzene,
4,4'-bis(trans-4-pentylcyclohexyl)-1,1'-ethylenedibenzene,
4-(trans-4-heptylcyclohexyl)-4'-trans-4-propylcyclohexyl)-1,1'-ethylenedibenzene,
4-[2-(trans-4-propylcyclohexyl)ethyl]-4'-(trans-4-ethylcyclohexyl)-1,1'-ethylenedibenzene,
4-[2-(trans-4-propylcyclohexyl)ethyl]-4'-(trans-4-propylcyclohexyl)-1,1'-ethylenedibenzene,
4-[2-(trans-4-propylcyclohexyl)ethyl]-4'-(trans-4-pentylcyclohexyl)-1,1'-ethylenedibenzene,
4-[2-(trans-4-propylcyclohexyl)ethyl]-4'-(trans-4-heptylcyclohexyl)-1,1'-ethylenedibenzene,
4-[2-(trans-4-butylcyclohexyl)ethyl]-4'-(trans-4-propylcyclohexyl)-1,1'-ethylenedibenzene,
4-[2-(trans-4-butylcyclohexyl)ethyl]-4'-(trans-4-pentylcyclohexyl)-1,1'-ethylenedibenzene,
4-[2-(trans-4-pentylcyclohexyl)ethyl]-4'-(trans-4-butylcyclohexyl)-1,1'-ethylenedibenzene,
4-[2-(trans-4-pentylcyclohexyl)ethyl]-4'-(trans-4-pentylcyclohexyl)-1,1'-ethylenedibenzene,
4-ethyl-4''-[2-(trans-4-propylcyclohexyl)ethyl]-p-terphenyl,
4-propyl-4''-[2-(trans-4-propylcyclohexyl)ethyl]-p-terphenyl,
4-butyl-4''-[2-(trans-4-pentylcyclohexyl)ethyl]p-terphenyl,
4-pentyl-4''-[2-(trans-4-propylcyclohexyl)ethyl]-p-terphenyl,
4-pentyl-4''-[2-(trans-4-butylcyclohexyl)ethyl]-p-terphenyl,
4-pentyl-4''-[2-trans-4-pentylcyclohexyl)ethyl]-p-terphenyl, 4-heptyl-4'''-[2-(trans-4-propylcyclohexyl)ethyl]p-terphenyl,
4-(trans-4-ethylcyclohexyl)-4'-[2-(p-(trans-4-propylcyclohexyl)phenyl)ethyl]biphenyl,
4-(trans-4-propylcyclohexyl)-4'-[2-(p-(trans-4-propylcyclohexyl)phenyl)ethyl]biphenyl,
4-(trans-4-butylcyclohexyl)-4'-[2-(p-(trans-4-pentylcyclohexyl)phenyl)ethyl]biphenyl,
4-(trans-4-pentylcyclohexyl)-4'-[2-(p-(trans-4-propylcyclohexyl)phenyl)ethyl]biphenyl,
4-(trans-4-pentylcyclohexyl)-4'-[2-(p-(trans-4-butylcyclohexyl)phenyl)ethyl]biphenyl,
4-(trans-4-pentylcyclohexyl)-4'-[2-(p-(trans-4-pentylcyclohexyl)phenyl)ethyl]biphenyl,
4-(trans-4-heptylcyclohexyl)-4'-[2-(p-(trans-4-propylcyclohexyl)phenyl)ethyl]biphenyl,
4-[2-(trans-4-propylcyclohexyl)ethyl]-4'-(p-ethylphenyl)-1,1'-ethylenedibenzene,
4-[2-(trans-4-propylcyclohexyl)ethyl]-4'-(p-propylphenyl)-1,1'-ethylenedibenzene,
4-[2-(trans-4-propylcyclohexyl)ethyl]-4'-(p-pentylphenyl)-1,1'-ethylenedibenzene,
4-[2-(trans-4-butylcyclohexyl)ethyl]-4'-(p-pentylphenyl)-1,1'-ethylenedibenzene,
4-[2-(trans-4-pentylcyclohexyl)ethyl]-4'-(p-butylphenyl)-1,1'-ethylenedibenzene and
4-[2-(trans-4-pentylcyclohexyl)ethyl]-4'-(p-pentylphenyl)-1,1'-ethylenedibenzene.

Especially preferred compounds of formula I are:
1-[2-(Trans-4-butylcyclohexyl)ethyl]-4-(trans-4-pentylcyclohexyl)benzene,
4-[2-(trans-4-butylcyclohexyl)ethyl]-4-(trans-4-pentylcyclohexyl)-1,1'-ethylenedibenzene and
4-(trans-4-pentylcyclohexyl)-4'-[2-(trans-4-butylcyclohexyl)ethyl]biphenyl.

The compounds of formula I can be manufactured in accordance with the following proceedure:

(a) for the manufacture of the compounds of formula I in which $R^1$ signifies trans-4-alkylcyclohexyl, 4'-alkyl-4-biphenylyl, p-(trans-4-alkylcyclohexyl)phenyl or 2-(trans-4-alkylcyclohexyl)ethyl and $R^2$ signifies trans-4-alkylcyclohexyl; or $R^1$ signifies trans-4-alkylcyclohexyl and $R^2$ signifies p-(trans-4-alkylcyclohexyl)phenyl, p-[2-(trans-4-alkylcyclohexyl)ethyl]phenyl or 4'-(trans-4-alkylcyclohexyl)-4-biphenylyl; or $R^1$ signifies p-alkylphenyl and $R^2$ signifies p-[2-(trans-4-alkylcyclohexyl)ethyl]phenyl, catalytically hydrogenating a compound of the formula

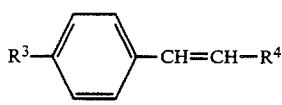

VII wherein $R^3$ signifies trans-4-alkylcyclohexyl, 4'-alkyl-4-biphenylyl, p-(trans-4-alkylcyclohexyl)phenyl or 2-(trans-4-alkylcyclohexyl)-ethyl and $R^4$ signifies trans-4-alkylcyclohexyl; or $R^3$ signifies trans-4-alkylcyclohexyl and $R^4$ signifies p-(trans-4-alkylcyclohexyl)phenyl, p-[2-(trans-4-alkylcyclohexyl)ethyl]phenyl or 4'-(trans-4-alkylcyclohexyl)-4-biphenylyl; or $R^3$ signifies p-alkylphenyl and $R^4$ signifies p-[2-(trans-4-alkylcyclohexyl)ethyl]phenyl, and the alkyl groups in the substituents $R^3$ and $R^4$ are straight-chain groups containing 1 to 7 carbon atoms, or (b) for the manufacture of the compounds of formula I in which $R^1$ signifies p-[2-(trans-4-alkylcyclohexyl)ethyl]phenyl and $R^2$ signifies trans-4-alkylcyclohexyl, reacting a compound of the formula

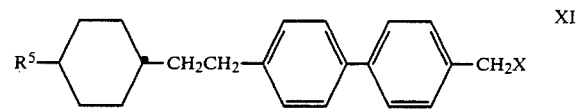

XI wherein $R^5$ signifies a straight-chain alkyl group containing 1 to 7 carbon atoms and X signifies a leaving group, with a compound of the general formula

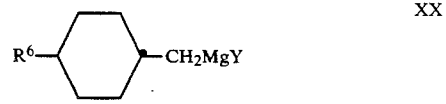

XX wherein $R^6$ signifies a straight-chain alkyl group containing 1 to 7 carbon atoms and Y signifies chlorine or bromine, in the presence of dilithium tetrachlorocuprate.

The catalytic hydrogenation of a compound of formula VII can be carried out according to known methods. Palladium is the preferred catalyst.

The reaction of a compound of formula XI with a compound of formula XX can be carried out according to known methods for the Fouquet-Schlosser coupling reaction. Leaving groups X include all conventional leaving groups which are usually used in such reactions. Preferred leaving groups are chlorine, bromine, iodine and the p-tosyloxy group, especially bromine. Y preferably signifies bromine.

The preparation of the starting materials of formulae VII and XI and preferred methods for the manufacture of the compounds of formula I are illustrated hereinafter in Reaction Schemes 1 and 2 in which $R^3$, $R^4$, $R^5$ and $R^6$ have the significances give above.

Scheme 1

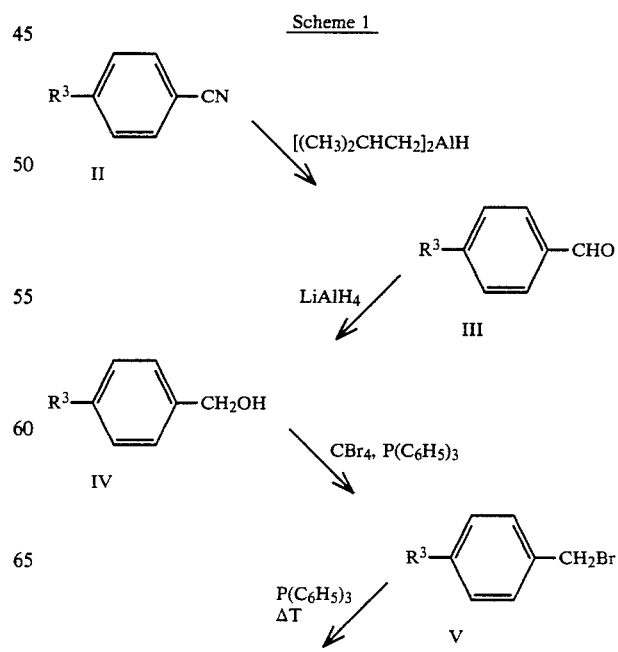

-continued
Scheme 1

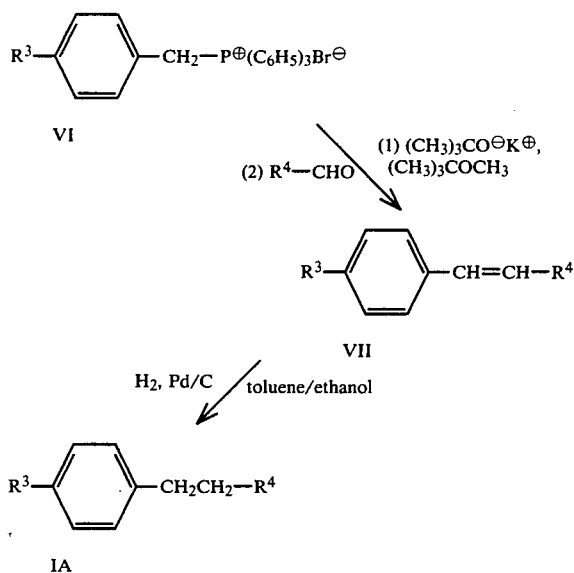

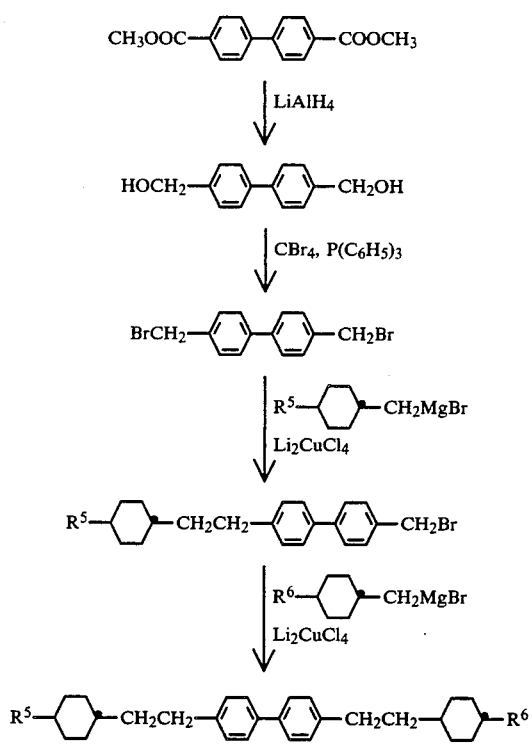

The compounds of the formula $R^4$-CHO in Scheme 1 can be obtained in a conventional manner from known compounds; for example, the trans-4-alkylcyclohexanecarboxaldehydes can be obtained by Rosenmund reduction of the corresponding acid chlorides and the remaining compounds can be obtained by reduction of the corresponding cyano compounds (in an analogous manner to the preparation of the compounds of formula III).

By reacting the compound of formula X with Grignard reagents in accordance with Scheme 2 there can be obtained compounds of formula XI or directly compounds of formula IB in which $R^5$ and $R^6$ have the same significance. When at least about 2 mol of Grignard reagent are used per mol of the compound of formula X a compound of formula IB is generally predominantly formed directly.

The compounds of formula I can be used in the form of mixtures with other liquid crystalline or non-liquid crystalline substances such as, for example, with substances from the classes of the Schiff's bases, azobenzenes, azoxybenzenes, phenylbenzoates, cyclohexanecarboxylic acid phenyl esters, cyclohexanecarboxylic acid cyclohexyl esters, biphenyls, terphenyls, phenylcyclohexanes, cinnamic acid derivatives, phenylpyrimidines, diphenylpyrimidines, cyclohexylphenylpyrimidines, phenyldioxanes, 2-cyclohexyl-1-phenylethanes and the like. Such substances are known to the person skilled in the art and many of them are, moreover, commercially available.

The liquid crystal mixtures in accordance with the invention contain, in addition to one or more compounds of formula I, preferably one or more of the following compounds:

4-Cyanobiphenyls of the formula

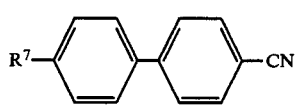

wherein $R^7$ is a straight-chain alkyl or alkoxy group containing 2 to 7 carbon atoms, p-(trans-4-alkylcyclohexyl)benzonitriles or p-(trans-4-alkylcyclohexyl)alkylbenzenes of the formula

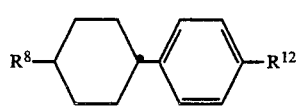

wherein $R^8$ is a straight-chain alkyl group of 2 to 7 carbon atoms and $R^{12}$ is cyano or a straight-chain alkyl group of 1 to 7 carbon atoms, p-(5-alkyl-2-pyrimidinyl)benzonitriles of the formula

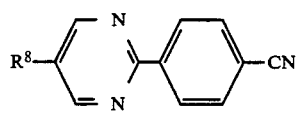

wherein $R^8$ has the above significance, p-[5-(trans-4-alkylcyclohexyl)-2-pyrimidinyl]benzonitriles of the formula

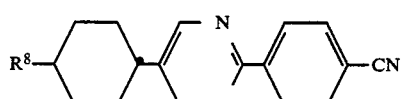

wherein $R^8$ has the above significance, p-(trans-5-alkyl-m-dioxan-2-yl)benzonitriles of the formula

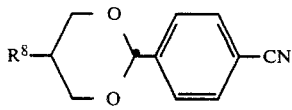

wherein $R^8$ has the above significance,
p-alkylbenzoic acid phenyl esters of the formula

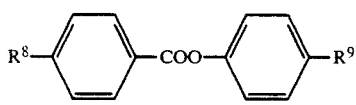

wherein $R^9$ is cyano or a straight-chain alkoxy group of 1 to 6 carbon atoms and $R^8$ has the above significance,
trans-4-alkylcyclohexanecarboxylic acid phenyl esters of the formula

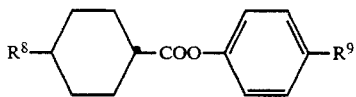

wherein $R^8$ and $R^9$ have the above significances,
2-(trans-4-alkylcyclohexyl)-1-phenylethanes of the formula

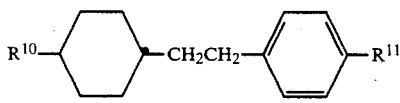

wherein $R^{10}$ is a straight-chain alkyl group of 3 to 7 carbon atoms and $R^{11}$ is cyano or a straight-chain alkyl or alkoxy group of 1 to 7 carbon atoms,
4''-alkyl-4-cyano-p-terphenyls of the formula

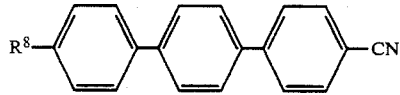

wherein $R^8$ has the above significance,
or 4'-(trans-4-alkylcyclohexyl)-4-cyanobiphenyls of the formula

wherein $R^8$ has the above significance.

The mixtures provided by the invention can contain one or more compounds of formula I. Preferably the mixtures contain one or more compounds of formula I in an amount of about 1 weight % to about 50 weight % and one or more other suitable liquid crystalline and/or non-liquid crystalline substances. Mixtures which contain about 3 weight % to about 30 weight % of compounds of formula I are especially preferred.

The mixtures provided by the invention can contain other suitable optically active compounds (e.g. optically active biphenyls) and/or dichroic colouring substances (e.g. azo, azoxy and anthraquinone colouring substances). The amount of such compounds is determined by the solubility and the desired pitch, colour, extinction and the like. Preferably, the amount of optically active compounds is at most about 4 weight % and the amount of dichroic colouring substance is at most about 10 weight %.

The manufacture of the liquid crystalline mixtures and of the electro-optical devices can be carried out in a known manner.

The invention is also concerned with all novel compounds, mixtures, processes, uses and devices as described herein.

The following Mixture Examples 1–11 are examples of preferred mixtures. The mixtures of Mixture Examples 5–8 are especially preferred. $\eta$ signifies the viscosity (bulk viscosity), $\Delta\epsilon$ signifies the dielectric anisotropy, $\Delta n$ signifies the optical anisotropy, $t_{on}$ signifies the switching-on time (0–50% transmission), $t_{off}$ signifies the switching-off time (100–10% transmission), $V_{10}$ and $V_{50}$ signify the threshold potential for 10% or 50% transmission (tilt angle 0°), $N_{max}$ signifies the maximum number of multiplexible lines, $k_{11}$(splay) and $k_{33}$ (bend) are elastic constants. All Mixture Examples were prepared as written.

MIXTURE EXAMPLE 1

Basic mixture A:
5.2 weight % of p-(5-pentyl-2-pyrimidinyl)benzonitrile,
11.5 weight % of p-(5-heptyl-2-pyrimidinyl)benzonitrile,
5.8 weight % of p-butylbenzoic acid p'-cyanophenyl ester,
12.2 weight % of trans-4-propylcyclohexanecarboxylic acid p-cyanophenyl ester,
12.4 weight % of trans-4-pentylcyclohexanecarboxylic acid p-cyanophenyl ester,
22.0 weight % of trans-4-butylcyclohexanecarboxylic acid p-ethoxyphenyl ester,
19.9 weight % of trans-4-pentylcyclohexanecarboxylic acid p-methoxyphenyl ester,
11.0 weight % of p-[5-(trans-4-ethylcyclohexyl)-2-pyrimidinyl]benzonitrile,
cl.p. 72.5° C., $\eta=42$ cp, nematic.

92 weight % of basic mixture A+8 weight % of 4-(trans-4-pentylcyclohexyl)-4'-[2-(trans-4-pentylcyclohexyl)ethyl]biphenyl; cl.p. 91° C., $\eta=43$ cp, nematic.

90 weight % of basic mixture A+10 weight % of 4,4'-bis[2-(trans-4-pentylcyclohexyl)ethyl]biphenyl; cl.p. 90.2° C., $\eta=43$ cp, nematic.

MIXTURE EXAMPLE 2

Basic mixture B:
4.1 weight % of p-(5-pentyl-2-pyrimidinyl)benzonitrile,
7.3 weight % of p-(5-heptyl-2-pyrmidinyl)benzonitrile,
14.0 weight % of trans-4-pentylcyclohexanecarboxylic acid p-methoxyphenyl ester,
22.9 weight % of trans-4-pentylcyclohexanecarboxylic acid p-propyloxyphenyl ester,
8.6 weight % of p-[5-(trans-4-ethylcyclohexyl)-2-pyrimidinyl]benzonitrile,
6.5 weight % of p-[5-(trans-4-pentylcyclohexyl)-2-pyrimidinyl]benzonitrile,
36.6 weight % of 2-(trans-4-pentylcyclohexyl)-1-(p-ethoxyphenyl)ethane; cl.p. 69.9° C., $\eta=26.3$ cp, nematic.

90 weight % of basic mixture B+10 weight % of 4-(trans-4-pentylcyclohexyl)-4'-[2-(trans-4-pentylcyclohexyl)ethyl]biphenyl; cl.p. 87° C., $\eta=27$ cp, nematic.

MIXTURE EXAMPLE 3

Basic mixture C:
6.3 weight % of p-(5-pentyl-2-pyrimidinyl)benzonitrile,
12.3 weight % of p-(5-heptyl-2-pyrimidinyl)benzonitrile,
22.0 weight % of trans-4-pentylcyclohexanecarboxylic acid p-methoxyphenyl ester,
30.2 weight % of trans-4-pentylcyclohexanecarboxylic acid p-propyloxyphenyl ester,
15.5 weight % of 2-(trans-4-heptylcyclohexyl)-1-(p-ethoxyphenyl)ethane,
13.7 weight % of trans-4-(p-pentylphenyl)cyclohexanecarboxylic acid trans-4-propylcyclohexyl ester; cl.p. 60.3° C., $\eta=30.0$ cp, nematic.
90 weight % of basic mixture C+10 weight % of 4-(trans-4-pentylcyclohexyl)-4'-[2-(trans-4-pentylcyclohexyl)ethyl]biphenyl; cl.p. 79√ C., $\eta=30.6$ cp, nematic.

MIXTURE EXAMPLE 4

Basic mixture D:
4.1 weight % of p-(5-pentyl-2-pyrimidinyl)benzonitrile,
8.2 weight % of p-(5-heptyl-2-pyrimidinyl)benzonitrile,
15.9 weight % of trans-4-pentylcyclohexanecarboxylic acid p-methoxyphenyl ester,
27.1 weight % of trans-4-pentylcyclohexanecarboxylic acid p-propyloxyphenyl ester,
24.7 weight % of 2-(trans-4-pentylcyclohexyl)-1-(p-ethoxyphenyl)ethane,
6.5 weight % of p-[5-(trans-4-pentylcyclohexyl)-2-pyrimidinyl]benzonitrile,
7.4 weight % of p-[(4a$\alpha$H, 8a$\beta$H)-decahydro-6$\beta$-propyl-2$\alpha$-naphthyl]benzonitrile (racemate),
6.1 weight % of p-[(4a$\alpha$H, 8a$\beta$H)-decahydro-6$\beta$-pentyl-2$\alpha$-napthyl]benzonitrile (racemate); cl.p. 68.9° C., $\eta=28.2$ cp, nematic.
90 weight % of basic mixture D+10 weight % of 4-(trans-4-pentylcyclohexyl)-4'-[2-(trans-4-pentylcyclohexyl)ethyl]biphenyl; cl.p. 87° C., $\eta=29$ cp, nematic.

MIXTURE EXAMPLE 5

3.89 weight % of 4'-propyl-4-cyanobiphenyl,
19.00 weight % of 4'-pentyl-4-cyanobiphenyl,
16.08 weight % of 2-(trans-4-propylcyclohexyl)-1-(p-ethoxyphenyl)ethane,
22.16 weight % of 2-(trans-4-pentylcyclohexyl)-1-(p-ethoxyphenyl)ethane,
5.72 weight % of 4''-pentyl-4-cyano-p-terphenyl,
5.83 weight % of 4'-(trans-4-pentylcyclohexyl)-4-cyanobiphenyl,
12.79 weight % of 1-[2-(trans-4-butylcyclohexyl)ethyl]-4-(trans-4-pentylcyclohexyl)benzene,
8.55 weight % of 4-[2-(trans-4-butylcyclohexyl)ethyl]-4'-(trans-4-pentylcyclohexyl)-1,1'-ethylenedibenzene,
5.98 weight % of 4-(trans-4-pentylcyclohexyl)-4'-[2-(trans-4-butylcyclohexyl)ethyl]biphenyl; m.p.$<-30°$ C., cl.p. 91.2° C., nematic; $\eta=24.8$ cp; $\Delta\epsilon=6.19$; $\Delta n=0.142$; $t_{on}=25$ ms, $t_{off}=40$ ms; $V_{10}=2.76$ V, $V_{50}=3.10$ V; $N_{max}=76$; $k_{33}/k_{11}=1.17$.

MIXTURE EXAMPLE 6

3.70 weight % of 4'-propyl-4-cyanobiphenyl,
18.09 weight % of 4'-pentyl-4-cyanobiphenyl,
15.32 weight % of 2-(trans-4-propylcyclohexyl)-1-(p-ethoxyphenyl)ethane,
21.10 weight % of 2-(trans-4-pentylcyclohexyl)-1-(p-ethoxyphenyl)ethane,
5.45 weight % of 4''-pentyl-4-cyano-p-terphenyl,
5.55 weight % of 4'-(trans-4-pentylcyclohexyl)-4-cyanobiphenyl,
12.18 weight % of 1-[2-(trans-4-butylcyclohexyl)ethyl]-4-(trans-4-pentylcyclohexyl)benzene,
8.14 weight % of 4-[2-(trans-4-butycyclohexyl)ethyl]-4'-(trans-4-pentylcyclohexyl)-1,1'-ethylenedibenzene,
5.70 weight % of 4-(trans-4-pentylcyclohexyl)-4'-[2-(trans-4-butylcyclohexyl)ethyl]biphenyl,
4.77 weight % of 1-propyl-4-(trans-4-pentylcyclohexyl)benzene; m.p. $<-30°$ C., cl.p. 88.2° C., nematic; $\eta=21.0$ cp; $\Delta\epsilon=5.84$; $\Delta n=0.140$; $t_{on}=24$ ms, $t_{off}=38$ ms; $V_{10}=2.75$ V, $V_{50}=3.08$ V; $N_{max}=78$; $k_{33}/k_{11}=1.05$.

MIXTURE EXAMPLE 7

3.23 weight % of 4'-propyl-4-cyanobiphenyl,
16.75 weight % of 4'-pentyl-4-cyanobiphenyl,
16.03 weight % of 2-(trans-4-propylcyclohexyl)-1-(p-ethoxyphenyl)ethane,
9.72 weight % of 2-(trans-4-propylcyclohexyl)-1-(p-butyloxyphenyl)ethane,
18.56 weight % of 2-(trans-4-pentylcyclohexyl)-1-(p-ethoxyphenyl)ethane,
4.75 weight % of 4''-pentyl-4-cyano-p-terphenyl,
4.84 weight % of 4'-(trans-4-pentylcyclohexyl)-4-cyanobiphenyl,
11.59 weight % of 1-[2-(trans-4-butylcyclohexyl)ethyl]-4-(trans-4-pentylcyclohexyl)benzene,
8.55 weight % of 4-[2-(trans-4-butylcyclohexyl)ethyl]-4'-(trans-4-pentylcyclohexyl)-1,1'-ethylenedibenzene,
5.98 weight % of 4-(trans-4-pentylcyclohexyl)-4'-[2-(trans-4-butylcyclohexyl)ethyl]biphenyl; m.p. $<-30°$ C., cl.p. 85.7, nematic; $\eta=21.5$ cp; $\Delta\epsilon=5.40$; $\Delta n=0.133$; $t_{on}=23$ ms, $t_{off}=37$ ms; $V_{10}=2.84$ V, $V_{50}=3.20$ V; $N_{max}=73$; $k_{33}/k_{11}=1.07$.

MIXTURE EXAMPLE 8

4.36 weight % of 4'-ethyl-4-cyanobiphenyl,
3.33 weight % of 4'-propyl-4-cyanobiphenyl,
16.49 weight % of 4'-pentyl-4-cyanobiphenyl,
15.67 weight % of 2-(trans-4-propylcyclohexyl)-1-(p-ethoxyphenyl)ethane.
6.36 weight % of 2-(trans-4-propylcyclohexyl)-1-(p-butyloxyphenyl)ethane,
18.19 weight % of 2-(trans-4-pentycyclohexyl)-1-(p-ethoxyphenyl)ethane,
4.90 weight % of 4''-pentyl-4-cyano-p-terphenyl,
4.98 weight % of 4'-(trans-4-pentylcyclohexyl)-4-cyanobiphenyl,
11.92 weight % of 1-[2-(trans-4-butylcyclohexyl)ethyl]-4-(trans-4-pentylcyclohexyl)benzene,
6.90 weight % of 4-[2-(trans-4-butylcyclohexyl)ethyl]-4'-(trans-4-pentylcyclohexyl)-1,1'-ethylenedibenzene,
6.90 weight % of 4-(trans-4-pentylcyclohexyl)-4'-[2-(trans-4-butylcyclohexyl)ethyl]biphenyl; m.p. $<-30°$ C., cl.p. 87.0° C., nematic; $\eta=24.0$ cp; $\Delta\epsilon=6.10$; $\Delta n=0.143$; $t_{on}=26$ ms, $t_{off}=43$ ms; $V_{10}=2.63$ V, $V_{50}=2.94$ V; $N_{max}=78$; $k_{33}/k_{11}=1.10$.

MIXTURE EXAMPLE 9

14.62 weight % of 4'-pentyl-4-cyanobiphenyl,
12.35 weight % of 4-hexyl-4-cyanobiphenyl, 14.48 weight % of 2-(trans-4-propylcyclohexyl)-1-(p-ethoxyphenyl)ethane,
7.98 weight % of 2-(trans-4-propylcyclohexyl)-1-(p-butyloxyphenyl)ethane,
15.96 weight % of 2-(trans-4-pentylcyclohexyl)-1-(p-ethoxyphenyl)ethane,
4.77 weight % of 4″-pentyl-4-cyano-p-terphenyl,
4.85 weight % of 4′-(trans-4-pentylcyclohexyl)-4-cyanobiphenyl,
10.46 % of 1-[2-(trans-4-butylcyclohexyl)ethyl]-4-(trans-4-pentylcyclohexyl)benzene,
8.55 weight % of 4-[2-(trans-4-butylcyclohexyl)ethyl]-4′-(trans-4-pentylcyclohexyl)-1,1′-ethylenedibenzene;
5.98 weight % of 4-(trans-4-pentylcyclohexyl)-4′-[2-(trans-4-butylcyclohexyl)ethyl]biphenyl; cl.p. 86.1° C., nematic.

MIXTURE EXAMPLE 10

14.02 weight % of 4′-pentyl-4-cyanobiphenyl,
11.84 weight % of 4′-hexyl-4-cyanobiphenyl,
13.89 weight % of 2-(trans-4-propylcyclohexyl)-1-(p-ethoxyphenyl)ethane,
7.66 weight % of 2-(trans-4-propylcyclohexyl)-1-(p-butyloxyphenyl)ethane,
15.30 weight % of 2-(trans-4-pentylcyclohexyl)-1-(p-ethoxyphenyl)ethane,
4.57 weight % of 4″-pentyl-4-cyano-p-terphenyl,
4.66 weight % of 4′-(trans-4-pentylcyclohexyl)-4-cyanobiphenyl,
10.03 weight % of 1-[2-(trans-4-butylcyclohexyl)ethyl]-4-(trans-4-pentylcyclohexyl)benzene,
9.83 weight % of 4-[2-(trans-4-butylcyclohexyl)ethyl]-4′-(trans-4-pentylcyclohexyl)-1,1′-ethylenedibenzene,
8.20 weight % of 4-[2-(trans-4-butylcyclohexyl)ethyl]-4′-(trans-4-propylcyclohexyl)-1,1′-ethylenedibenzene; nematic.

MIXTURE EXAMPLE 11

4.29 weight % of 4′-ethyl-4-cyanobiphenyl,
3.27 weight % of 4′-propyl-4-cyanobiphenyl,
16.21 weight % of 4′-pentyl-4-cyanobiphenyl,
15.41 weight % of 2-(trans-4-propylcyclohexyl)-1-(p-ethoxyphenyl)ethane,
6.26 weight % of 2-(trans-4-propylcyclohexyl)-1-(p-butyloxyphenyl)ethane,
17.88 weight % of 2-(trans-4-pentycyclohexyl)-1-(p-ethoxyphenyl)ethane,
4.81 weight % of 4″-pentyl-4-cyano-p-terphenyl,
4.90 weight % of 4′-(trans-4-pentylcyclohexyl)-4-cyanobiphenyl,
11.72 weight % of 1-[2-(trans-4-butylcyclohexyl)ethyl]-4-(trans-4-pentycyclohexyl)benzene,
8.47 weight % of 4-[2-(trans-4-butylcyclohexyl)ethyl]-4′-(trans-4-pentylcyclohexyl)-1,1′-ethylenedibenzene,
6.78 weight % of 4-[2-(trans-4-butylcyclohexyl)ethyl]-4′-(trans-4-propylcyclohexyl)-1,1′-ethylenedibenzene; nematic.

The following examples illustrate the manufacture of the inventive compounds. In the examples, C denotes a crystalline phase, S denotes a smectic phase, N denotes a nematic phase and I denotes the isotropic phase. Unless otherwise stated, percentages and ratios relating to solvent mixtures are expressed in volume, purity data determined by gas chromatography are expressed in area % and the remaining percentages and ratios are expressed in weight, temperatures are in degrees Celsius (°C.), normal pressure is about 1 atmosphere and room temperature is about 23° C. The petroleum ether is a well-known mixture of low-boiling hydrocarbons. Unless indicated otherwise, the examples were carried out as written.

EXAMPLE 1

2.20 g of 4-(trans-4-pentylcyclohexyl)-4′-[2-(trans-4-pentylcyclohexyl)vinyl]biphenyl were suspended in a toluene/ethanol mixture (3:2) in a sulphonation flask, treated with 200 mg of palladium/carbon (10%) and hydrogenated at normal pressure and 50° C. until the hydrogen uptake came to a standstill. Filtration of the mixture and concentration of the filtrate gave a white, semi-crystalline residue which, after recrystallization from 100 ml of hexane, yielded 1.55 g of 4-(trans-4-pentylcyclohexyl)-4′-[2-(trans-4-pentylcyclohexyl)ethyl]biphenyl as colourless needles; transition (presumably S-S) 219.5° C., transition S-N 243.2° C., cl.p. (N-I) 256.1° C. This substance showed itself to be very considerably super-coolable; it did not crystallize upon cooling to room temperature. Rf value (hexane): 0.32.

The 4-(trans-4-pentylcyclohexyl)-4′-[2-(trans-4-pentylcyclohexyl)vinyl]biphenyl used as the starting material was prepared as follows:

(a) A solution of 10.0 g of 4′-(trans-4-pentylcyclohexyl)-4-biphenylcarbonitrile in 150 ml of methylene chloride was placed at −35° C. in a sulphonation flast while gassing with argon and treated within 8 minutes with 40 ml of an about 1.5N solution of diisobutylaluminium hydride in toluene. After completion of the addition, the mixture was stirred for 2 hours at −35° C. and then for a further 1.5 hours with gradual warming to 0° C., before it was treated cautiously with 100 ml of 1N sulphuric acid and extracted three times with 150 ml of diethyl ether each time. The organic phases were washed with 100 ml of 1N sulphuric acid, twice with 100 ml of water each time and once with 100 ml of saturated sodium chloride solution, dried over magnesium sulphate and concentrated. There were obtained 9.5 g (95%) of 4′-(trans-4-pentylcyclohexyl)-4-biphenylcarboxaldehyde as a colourless, crystalline mass (m.p. 115°–116° C.) which was used in the following step without further purification. Rf value [toluene/ethyl acetate (19:1)]: educt 0.65, product 0.52.

(b) A mixture of 930 mg of lithium aluminium hydride in 100 ml of absolute tetrahydrofuran was placed at 0° C. in a sulphonation flask and treated within 20 minutes with a solution of 8.2 g of 4′-(trans-4-pentylcyclohexyl)-4-biphenylcarboxaldehyde in 100 ml of absolute tetrahydrofuran. After completion of the addition, the mixture was stirred for a further 2 hours while warming to room temperature, subsequently cautiously quenched with 100 ml of 1N sulphuric acid and extracted three times with 200 ml of methylene chloride each time. The organic phases were washed twice with 100 ml of water each time, dried over magnesium sulphate and concentrated. There were obtained 7.90 g (96%) of 4′-(trans-4-pentylcyclohexyl)-4-biphenylmethanol as a colourless, crystalline mass (purity 99.4% in accordance with gas chromatography) which was used in the following step without further purification. M.p. 180.4° C.; Rf value [petroleum ether/ethyl acetate (9:1)]: educt 0.70, product 0.30.

(c) A mixture of 3.5 g of 4′-(trans-4-pentylcyclohexyl)-4-biphenylmethanol and 2.9 g of triphenylphosphine in 150 ml of absolute methylene chloride was placed at −20° C. in a sulphonation flask while gassing with argon and treated portionwise within 10 minutes with 3.8 g of solid tetrabromomethane. Partially undissolved educt thereby dissolved slowly. The mixture was stirred for a further 2 hours while warming to room temperature. The mixture was subsequently concentrated on a rotary evaporator and the crystalline residue was suspended in 300 ml of warm hexane, freed by filtration from precipitated triphenylphosphine oxide (rinsing with hexane) and the filtrate was concentrated. Low-pressure chromatography (0.7 bar) of the residue on silica gel with toluene as the eluant gave 3.39 g (82%) of 4-(bromomethyl)-4'-(trans-4-pentylcyclohexyl)biphenyl as colourless crystals. This material was used in the following step without further purification. Rf value of the product [petroleum ether/ethyl acetate (97:3)]: 0.47.

(d) A mixture of 2.63 g of 4-(bromomethyl)-4'-(trans-4-pentylcyclohexyl)biphenyl and 2.2 g of triphenylphosphine in 150 ml of o-xylene was heated to reflux (bath temperature 160° C.) for 15 hours in a sulphonation flask while gassing with argon. After cooling, the white precipitate formed was filtered off, washed several times with benzene and dried in a high vacuum (0.1 mmHg) at 80° C. for 1 hour. There were obtained 3.48 g (80%) of [[4'-(trans-4-pentylcyclohexyl)-4-biphenylyl]methyl]triphenylphosphonium bromide as a white powder (m.p. 263°–265° C.) which was used in the following Wittig reaction without further purification.

(e) A mixture of 3.31 g of [[4'-(trans-4-pentylcyclohexyl)-4-biphenylyl]methyl]triphenylphosphonium bromide in 50 ml of t-butyl methyl ether was placed at 0° C. in a sulphonation flask while gassing with argon and treated with 617 mg of solid potassium t-butylate. After completion of the addition, the mixture was stirred at 0° C. for a further 15 minutes (a deep orange colouration resulting) and then treated within 10 minutes at 0° C. with a solution of 912 mg of trans-4-pentylcyclohexanecarboxaldehyde in 20 ml of t-butyl methyl ether. The mixture was subsequently stirred at 0° C. for a further 30 minutes and at room temperature for 90 minutes and then the yellow mixture was poured into 150 ml of water and extracted three times with 150 ml of diethyl ether each time. The organic phases were washed twice with 100 ml of water each time, dried over magnesium sulphate and concentrated. Low-pressure chromatography (0.7 bar) of the residue on silica gel with toluene as the eluant gave 2.43 g (100%) of 4-(trans-4-pentylcyclohexyl)-4'-[2-(trans-4-pentylcyclohexyl)vinyl]biphenyl as a colourless, crystalline mass. This material was used without further purification in the hydrogenation described in the first paragraph of this Example. Rf values of the product (hexane): 0.29 and 0.32 (cis/trans mixture).

The following compounds can be manufactured in an analogous manner:

4-(Trans-4-pentylcyclohexyl)-4'-[2-(trans-4-propylcyclohexyl)ethyl]biphenyl; transition S-S 208.1° C., transition S-N 234.0° C., cl.p. (N-I) 263.5° C.;

4-(trans-4-pentylcyclohexyl)-4'-[2-(trans-4-butylcyclohexyl)ethyl]biphenyl; transition S-S 215.9° C., transition S-N 240° C., cl.p. (N-I) 259° C.;

4-[2-(trans-4-butylcyclohexyl)ethyl]-4'-(trans-4-propylcyclohexyl)-1,1'-ethylenedibenzene; m.p. (C-S) 68.9° C., transition S-S 117.5° C., transition S-N 171.5° C., cl.p. (N-I) 187.3° C.;

4-[2-(trans-4-butylcyclohexyl)ethyl]-4'-(trans-4-pentylcyclohexyl)-1,1'-ethylenedibenzene; m.p. (C-S) 48.0° C., cl.p. (S-I) 188.0° C.;

4-(trans-4-pentylcyclohexyl)-4'-[2-(p-(trans-4-butylcyclohexyl)phenyl)ethyl]biphenyl; m.p. 65° C., cl.p. 331.6° C.;

4-(trans-4-pentylcyclohexyl]-4'-[2-(p-(trans-4-pentylcyclohexyl)phenyl)ethyl]biphenyl; cl.p. 323.5° C.;

4-(trans-4-pentylcyclohexyl)-4'-(trans-4-propylcyclohexyl)-1,1'-ethylenedibenzene; m.p. (C-S) 116.8° C., transition S-N 198.5° C., cl.p. (N-I) 221.9° C.;

4-pentyl-4''-[2-(trans-4-butylcyclohexyl)ethyl]-p-terphenyl; m.p. (C-S) 149.8° C., transition S-S 215.5° C., transition S-N 263° C., cl.p. (N-I) 267° C.;

4-[2-(trans-4-butylcyclohexyl)ethyl]-4'-(p-pentylphenyl)-1,1'-ethylenedibenzene; m.p. (C-S) 0° C., transition S-S 76.5° C., cl.p. (S-I) 194° C.;

1-[2-(trans-4-butylcyclohexyl)ethyl]-4-(trans-4-pentylcyclohexyl)benzene; m.p. (C-S) 28.1° C., cl.p. (S-I) 138.4° C.;

1-[2-(trans-4-pentylcyclohexyl)ethyl]-4-(trans-4-propylcyclohexyl)benzene; m.p. (C-S) 40.2° C., transition S-N 126° C., cl.p. (N-I) 132.7° C.; and 1-[2-(trans-4-butylcyclohexyl)ethyl]-4-[2-(trans-4-pentylcyclohexyl)ethyl]benzene; m.p. (C-S) 10.4 or 21.6° C. (2 modifications), cl.p. (S-I) 125.8° C.

EXAMPLE 2

(a) A suspension of 2.14 g of 4,4'-bis(hydroxymethyl)biphenyl (prepared by reducing dimethyl biphenyl-4,4'-dicarboxylate with lithium aluminium hydride) and 5.5 g of triphenylphosphine in 60 ml of methylene chloride was placed at −10° C. in a sulphonation flask while gassing with argon and treated within 3 minutes with 7.3 g of tetrabromoethane. After completion of the addition, the mixture was stirred for a further 16 hours with gradual warming to +10° C. and then, after concentration on a rotary evaporator, triturated with hot benzene. Filtration and concentration gave 12.67 g of crude product which, after low-pressure chromatography (0.5 bar) with toluene on silica gel, yielded 2.60 g (76%) of 4,4'-bis(bromomethyl)biphenyl. A recrystallization from 50 ml of acetone gave 1.78 g of the dibromide as colourless crystals of melting point 172.8° C. Rf value [hexane/toluene (2:1)]: 0.41.

(b) 122 mg of magnesium shavings were covered with 3 ml of absolute tetrahydrofuran in a sulphonation flask while gassing with argon and, after the addition of a crystal of iodine, treated with a solution of 1.24 g of trans-1-(bromomethyl)-4-pentylcyclohexane in 7 ml of absolute tetrahydrofuran. After completion of the addition the mixture was heated to reflux for a further 30 minutes and then the mixture, cooled to −78° C., was treated in sequence with 0.7 ml of a 0.1N solution of dilithium tetrachlorocuprate in tetrahydrofuran and with a solution of 670 mg of 4,4'-bis(bromomethyl)biphenyl in 10 ml of absolute tetrahydrofuran. The yellow colouration which initially appeared disappeared again after a few minutes. The mixture, warmed to −15° C., was subsequently stirred for a further 17 hours, then treated with 25 ml of 2N hydrochloric acid and extracted three times with 50 ml of diethyl ether each time. The organic phases were washed with 50 ml of saturated sodium chloride solution, dried over magnesium sulphate and concentrated. Low-pressure chromatography (0.5 bar) of the residue (1.06 g) on silica gel with hexane and subsequently hexane/diethyl ether (19:1) as the eluant gave in succession 1,1'-ethylene-bis(trans-4-pentylcyclohexane), 228 mg (22%) of 4,4'-bis[2-(trans-4-pentylcyclohexyl)ethyl]biphenyl, 78 mg (9%) of 4-(bromomethyl)-4'-[2-(trans-4-pentylcyclohexyl)ethyl]biphenyl and 4,4'-bis(bromomethyl)biphenyl. A single crystallization of the 228 mg of 4,4'-bis[2-(trans-4-pentylcyclohexyl)ethyl]biphenyl from hexane yielded 194 mg of colourless needles of clearing point >300° C. (further phase transitions at 68° C., 84° C., 161° C., 203° C., 221° C. and 224° C.). Rf values (hexane): 4,4,-bis(bromomethyl)biphenyl 0.14; 4-(bromomethyl)-4'-[2-(trans-4-pentylcyclohexyl)ethyl]biphenyl 0.24; 4,4'-bis[2-(trans-4-pentylcyclohexyl)ethyl]biphenyl 0.40.

We claim:

1. A compound of the formula

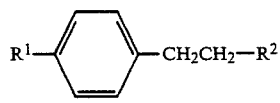

wherein $R^1$ is trans-4-alkylcyclohexyl, 4'-alkyl-4-biphenylyl, p-(trans-4-alkylcyclohexyl)phenyl, 2-(trans-4-alkylcyclohexyl)ethyl or p-[2-(trans-4-alkylcyclohexyl)ethyl]phenyl and $R^2$ is trans-4-alkylcyclohexyl; or $R^1$ is trans-4-alkylcyclohexyl and $R^2$ is p-(trans-4-alkylcyclohexyl)phenyl, p-[2-(trans-4-alkylcyclohexyl)ethyl]phenyl or 4'-(trans-4-alkylcyclohexyl)-4-biphenylyl; or $R^1$ is p-alkylphenyl and $R^2$ is p-[2-(trans-4-alkylcyclohexyl)ethyl]phenyl, and the alkyl groups in the substituents $R^1$ and $R^2$ are straight-chain groups of 1 to 7 carbon atoms.

2. The compound of claim 1 wherein $R^1$ is trans-4-alkylcyclohexyl, 4'-alkyl-4-biphenylyl, p-(trans-4-alkylcyclohexyl)phenyl, 2-(trans-4-alkylcyclohexyl)ethyl or p-[2-(trans-4-alkylcyclohexyl)ethyl]phenyl and $R^2$ is trans-4-alkylcyclohexyl.

3. The compound of claim 1 wherein $R^1$ is trans-4-alkylcyclohexyl and $R^2$ is p-(trans-4-alkylcyclohexyl)phenyl, p-[2-(trans-4-alkylcyclohexyl)ethyl]phenyl or 4'-(trans-4-alkylcyclohexyl)-4-biphenylyl.

4. The compound of claim 1 wherein $R^1$ is p-alkylphenyl and $R^2$ is p-[2-(trans-4-alkylcyclohexyl)ethyl]phenyl.

5. The compound of claim 1 wherein $R^1$ is trans-4-alkylcyclohexyl, p-(trans-4-alkylcyclohexyl)phenyl, 2-(trans-4-alkylcyclohexyl)ethyl or p-[2-(trans-4-alkylcyclohexyl)ethyl]phenyl and $R^2$ is trans-4-alkylcyclohexyl; or $R^1$ is trans-4-alkylcyclohexyl and $R^2$ is p-(trans-4-alkylcyclohexyl)phenyl or p-[2-(trans-4-alkylcyclohexyl)ethyl]phenyl.

6. The compound of claim 1 wherein $R^1$ and $R^2$ are trans-4-alkylcyclohexyl.

7. The compound of claim 1 wherein $R^1$ is 4'-alkyl-4-biphenylyl and $R^2$ is trans-4-alkylcyclohexyl.

8. The comound of claim 1 wherein $R^1$ is p-(trans-4-alkylcyclohexyl)phenyl and $R^2$ is trans-4-alkylcyclohexyl.

9. The compound of claim 1 wherein $R^1$ is trans-4-alkylcyclohexyl and $R^2$ is 4'-(trans-4-alkylcyclohexyl)-4-biphenylyl.

10. The compound of claims 1, 2, 3, 4, 5 or 6 wherein the sum of the carbon atoms in the alkyl groups of the substituents $R^1$ and $R^2$ is 5 to 10.

11. The compound of claim 1, 1-[2-(trans-4-butylcyclohexyl)ethyl]-4-(trans-4-pentylcyclohexyl)benzene.

12. The compound of claim 1, 4-[2-(trans-4-butylcyclohexyl)ethyl]-4'-(trans-4-pentylcyclohexyl)-1,1'-ethylenedibenzene.

13. The compound of claim 1, 4-(trans-4-pentylcyclohexyl)-4'-[2-(trans-4-butylcyclohexyl)ethyl]biphenyl.

14. A liquid crystalline mixture comprising at least two components wherein at least one of said components is a compound of the formula

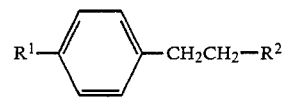

wherein $R^1$ is trans-4-alkylcyclohexyl, 4'-alkyl-4-biphenylyl, p-(trans-4-alkylcyclohexyl)phenyl, 2-(trans-4-alkylcyclohexyl)ethyl or p-[2-(trans-4-alkylcyclohexyl)ethyl]phenyl and $R^2$ is trans-4-alkylcyclohexyl; or $R^1$ is trans-4-alkylcyclohexyl and $R^2$ is p-(trans-4-alkylcyclohexyl)phenyl, p-[2-(trans-4-alkylcyclohexyl)ethyl]phenyl or 4'-(trans-4-alkylcyclohexyl)-4-biphenylyl; or $R^1$ is p-alkylphenyl and $R^2$ is p-[2-(trans-4-alkylcyclohexyl)ethyl]phenyl, and the alkyl groups in the substituents $R^1$ and $R^2$ are straight-chain groups of 1 to 7 carbon atoms.

15. The liquid crystalline mixture of claim 14 comprising one or more compounds of formula I and one or more compounds of the formulae

XII

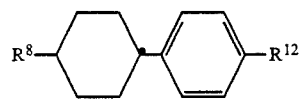

XIII

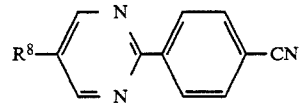

XIV

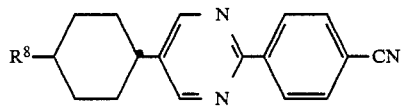

XV

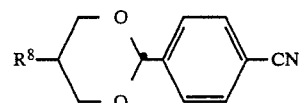

XVI

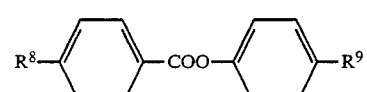

XVII

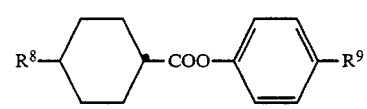

XVIII

-continued

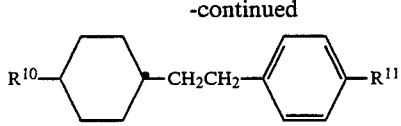

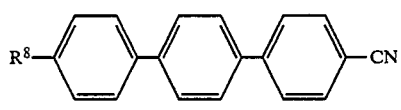

or

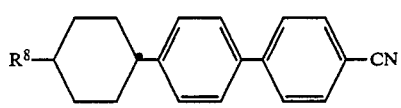

wherein R⁷ is a straight-chain alkyl or alkoxy group of 2 to 7 carbons atoms, R⁸ is a straight-chain alkyl group of 2 to 7 carbon atoms, R⁹ is cyano or a straight-chain alkoxy group of 1 to 6 carbon atoms, R¹⁰ is a straight-chain alkyl group of 3 to 7 carbon atoms, R¹¹ is cyano or a straight-chain alkyl or alkoxy group of 1 to 7 carbon atoms and R¹² is cyano or a straight-chain alkyl group of 1 to 7 carbon atoms.

16. The liquid crystalline mixture of claim 14 comprising 4'-propyl-4-cyanobiphenyl, 4'-pentyl-4-cyanobiphenyl, 2-(trans-4-propylcyclohexyl)-1-(p-ethoxyphenyl)ethane, 2-(trans-4-pentylcyclohexyl)-1-(p-ethoxyphenyl)ethane, 4''-pentyl-4-cyano-p-terphenyl, 4'-(trans-4-pentylcyclohexyl)-4-cyanobiphenyl, 1-[2-(trans-4-butylcyclohexyl)ethyl]-4-(trans-4-pentylcyclohexyl)benzene, 4-[2-(trans-4-butylcyclohexyl)ethyl]-4'-(trans-4-pentylcyclohexyl)-1,1'-ethylenedibenzene and 4-(trans-4-pentylcyclohexyl)-4'-[2-(trans-4-butylcyclohexyl)ethyl]biphenyl.

17. In an improved electro-optical cell having two plate means, liquid crystal means disposed between the two plate means and means for applying an electrical potential to said plate means, the improvement comprising the liquid crystal means including a compound of the formula

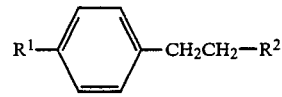

wherein R¹ is trans-4-alkylcyclohexyl, 4'-alkyl-4-biphenylyl, p-(trans-4-alkylcyclohexyl)phenyl, 2-(trans-4-alkylcyclohexyl)ethyl or p-[2-(trans-4-alkylcyclohexyl)ethyl]phenyl and R² is trans-4-alkylcyclohexyl; or R¹ is trans-4-alkylcyclohexyl and R² is p-(trans-4-alkylcyclohexyl)phenyl, p-[2-(trans-4-alkylcyclohexyl)ethyl]phenyl or 4'-(trans-4-alkylcyclohexyl)-4-biphenyl; or R¹ is p-alkylphenyl and R² is p-[2-(trans-4-alkylcyclohexyl)ethyl]phenyl, and the alkyl groups in the substituents R¹ and R² are straight-chain groups of 1 to 7 carbon atoms.

* * * * *

UNITED STATES PATENT AND TRADEMARK OFFICE
CERTIFICATE OF CORRECTION

PATENT NO. : 4,583,826
DATED : April 22, 1986
INVENTOR(S) : Petrzilka, et al.

It is certified that error appears in the above—identified patent and that said Letters Patent is hereby corrected as shown below:

Cover page, left column under Foreign Application Priority Data:

October 19, 1981 should be October 14, 1981

*Signed and Sealed this*

*Eighth Day of July 1986*

[SEAL]

*Attest:*

*Attesting Officer*

DONALD J. QUIGG

*Commissioner of Patents and Trademarks*